United States Patent [19]

Kohn et al.

[11] Patent Number: 5,099,060
[45] Date of Patent: Mar. 24, 1992

[54] SYNTHESIS OF AMINO ACID-DERIVED BIOERODIBLE POLYMERS

[75] Inventors: Joachim B. Kohn, Highland Park; Satish K. K. Pulapura, Piscataway, both of N.J.

[73] Assignee: Rutgers, The State University of New Jersey, New Brunswick, N.J.

[21] Appl. No.: 536,425

[22] Filed: Jun. 12, 1990

[51] Int. Cl.⁵ .......................................... C07C 229/00
[52] U.S. Cl. ................................................. 560/40
[58] Field of Search ........................................ 560/40

[56] References Cited

U.S. PATENT DOCUMENTS 4,579,866  4/1986  Stevenson et al. .................. 560/40

OTHER PUBLICATIONS

Proceed. Intern. Symp. Control. Rel. Bioact. Mater., 16, 115-6 (1978).

Primary Examiner—Bruce Gray
Attorney, Agent, or Firm—Lerner, David, Littenberg, Krumholz & Mentlik

[57] ABSTRACT

Novel amino acid-derived polycarbonates and amino acid-derived diphenol compound starting materials from which the polycarbonates are polymerized. Polymer blends of the amino acid-derived polycarbonates with polyiminocarbonates prepared from identical amino acid-derived diphenol starting materials.

2 Claims, 1 Drawing Sheet

SYNTHESIS OF AMINO ACID-DERIVED BIOERODIBLE POLYMERS

DESCRIPTION

BACKGROUND OF THE INVENTION

The present invention relates to amino acid-derived bioerodible polymers and to methods of synthesizing such polymers.

Co-pending Pat. application Ser. No. 219,290 describes new polyiminocarbonates useful as degradable polymers in general, and as tissue compatible bioerodible materials for biomedical uses. That application also discloses several new methods for synthesizing polyiminocarbonates. The disclosure of polyiminocarbonates and methods of synthesizing polyiminocarbonates in said U.S. Pat. application Ser. No. 219,290 is hereby incorporated herein by reference thereto.

According to U.S. Pat. application Ser. No. 219,290, polyiminocarbonates are structurally related to polycarbonates. The polyiminocarbonates have imino groups in the places normally occupied by carbonyl oxygen in the polycarbonates. This modification of the polymer backbone imparts a significant degree of hydrolytic instability to the polymer. The hydrolytic instability is desirable because it renders the polymer biodegradable and provides gradual erosion of the polymer within the body when the polyiminocarbonate is used as an implanted medical device. Yet, polyiminocarbonates retain some of the good mechanical properties of corresponding polycarbonates, in particular, mechanical strength.

One preferred species of polyiminocarbonates disclosed by U.S. Pat. application Ser. No. 219,290 has amino acid-based repeating structural units with Formula I:

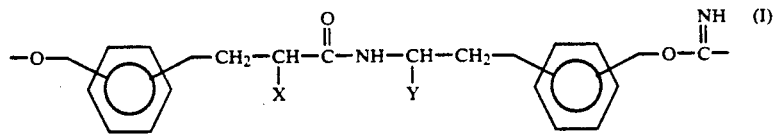

wherein X is

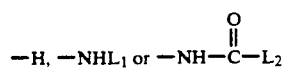

with $L_1$ being any one of the commonly used N-terminus protecting groups used in peptide synthesis including those disclosed in Bodanszky, *The Practice of Peptide Synthesis* (Springer-Verlag, NY, 1984), the disclosure of which is herein incorporated by reference thereto; and $L_2$ being a straight or branched alkyl chain; and Y being hydrogen or a C-terminus protecting group:

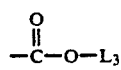

as also disclosed by Bodanszky, which disclosure is also herein incorporated by reference thereto, with $L_3$ being an alkyl, aryl or alkylaryl group and preferably a hexyl group. The preferred N-terminus protecting groups were benzyloxycarbonyl and tert-butoxycarbonyl groups.

The above polymers are essentially iminocarbonate-amides with pendent chains attached to the polymer backbone. Such polyiminocarbonates are prepared by reacting an amino acid-derived diphenol with an amino acid-derived dicyanate.

In Kohn, U.S. Pat. No. 4,638,045, poly(amino acid iminocarbonates) are disclosed that possess suitable tissue compatibility and bioerodibility properties for biomedical uses. These polymers, however, are impractical in certain applications because they lack suitable mechanical properties, in particular, ductility. The amino acid-derived polyiminocarbonates of U.S. Pat. application Ser. No. 219,290 were disclosed to possess a higher molecular weight and therefore better mechanical properties.

The drawback to polyiminocarbonates, however, is that the imino group is heat sensitive with thermal decomposition temperatures ($T_d$) close to the lowest possible processing temperature. The polyiminocarbonates of U.S. Pat. application Ser. No. 219,290 and U.S. Pat. No. 4,638,045 became soft enough for compression molding about 20° to 60° C. above their glass transition temperature $T_g$, which temperatures are close to or above their $T_d$, which is determined by the intrinsic properties of the iminocarbonate linkage.

Consequently, the practical applicability of most polyiminocarbonates is limited by the fact that conventional fabrication techniques such as compression molding, extrusion or injection molding cannot be applied without simultaneous decomposition of the polymer. The lack of detailed studies relating the monomer structure to the physicomechanical properties of the corresponding polymer made it difficult to identify more heat stable polyiminocarbonates among the numerous molecular structures claimed in the '290 application and in U.S. Pat. No. 4,638,045.

SUMMARY OF THE INVENTION

The need for hydrolytically unstable polmers having improved thermal stability is met by the present invention. It has now been discovered that the N-terminus protecting group of amino acid-derived polyiminocarbonates raises the $T_g$ of the polymers while the C-terminus protecting group lowers the $T_g$ to the polymers. This was completely unexpected and contrary to the conventional wisdom that both types of terminal groups would reduce the polymer $T_g$. Instead, $T_g$ is minimized when the N-terminus is completely removed. The $T_g$ is also unacceptable high when both the N-terminus and C-terminus are removed. However, when the N-terminus is removed and the C-terminus is present with a suitable protecting group attached, the $T_g$ of the resulting polyiminocarbonate is low enough to permit compression molding of the polymer. Referring to Formula I, the $T_g$ of amino acid-derived polyiminocarbonates is minimized when X is hydrogen and Y is:

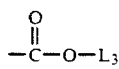

with $L_3$ being a straight chain alkyl group containing 2 to 18 carbon atoms.

Attendant with this discovery, it was also learned that amino acid-derived polyiminocarbonates degraded significantly more rapidly than polyiminocarbonates derived from Bisphenol A and similar conventional monomers. This lead to the preparation and investigation of amino acid-derived polycarbonates, which, it was unexpectedly discovered, degraded under physiological conditions, albeit at a slower rate than polyiminocarbonates. Since the amino acid-derived polycarbonates lack the imino group, the $T_d$'s of these polymers are significantly higher than the $T_d$'s of their polyiminocarbonate counter parts. Thus, the amino acid-derived polycarbonates can not only be compression molded, but also injection molded without thermal decomposition.

Therefore, according to one aspect of the present invention, monomers are provided that are capable of being polymerized to form polyiminocarbonates with $T_g$'s sufficiently low to permit thermal processing. The monomers provided by this aspect of the present invention are diphenol compounds that are amino acid derivatives of Formula II:

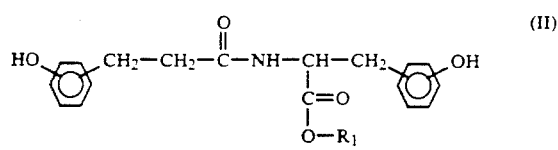

in which $R_1$ is an alkyl group containing up to 18 carbon atoms.

According to another aspect of the present invention, the same amino acid-derived monomers are polymerized to high molecular weight polycarbonates that have repeating structural units according to Formula III:

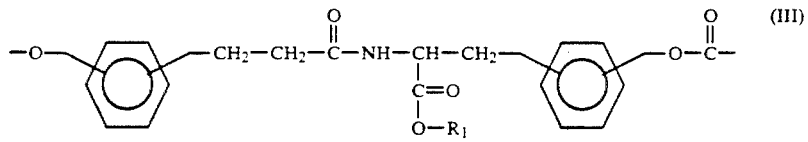

in which $R_1$ is as discussed above with respect to Formula II. Amino acid-derived polycarbonates according to this aspect of the present invention have intrinsic viscosities above about 0.6 dL/g (chloroform, 30° C.) corresponding to weight-average molecular weights typically above about 150,000 daltons and higher, as calculated from gel permeation chromatography relative to polystyrene standards without further correction.

According to a third aspect of the present invention, polymer blends of polycarbonates and polyiminocarbonates are provided, prepared from the amino acid-derived monomers of the present invention, wherein both polymer components of the blend are each derived from the same monomeric starting material. The two polymer components form highly compatible blends because they are derived from the same monomeric starting material. Furthermore, because the toxicology and biocompatibility of only one monomer needs to be investigated, the requirements for establishing the biocompatibility of the polymer blends of the present invention are simplified, as compared to copolymers or polymer blends prepared from different monomeric starting materials.

While not being bound by any particular theory, it is believed that the amino acid-derived polycarbonates first degrade by simple hydrolysis of the side chain ester bonds, which generates polar carboxylic acid groups. These polar groups increase the solubility of the polymer and lead to either swelling or partial solubilization of individual polymer chains. At this point, further hydrolytic cleavage of the polymer backbone, or possibly enzymatic degradation in vivo, at the amide linkages are believed to result in the ultimate degradation of the polymer. In addition, the amino acid-derived degradation products appear to be highly tissue compatible. The amino acid-derived polycarbonates of the present invention represent a major improvement in the design of polymeric biomaterials. Due to the carefully optimized structure of the amino acid-derived monomers of Formula II, the resulting polycarbonates according to Formula III combine degradability, tissue compatibility, processibility and favorable material and engineering properties (such as high tensile strength and high tensile modulus). Never before have all four of these properties been combined in polycarbonate or polyiminocarbonate type polymers.

The amino acid-derived polycarbonates are hydrolytically and thermally more stable than the corresponding polyiminocarbonates of U.S. Pat. application Ser. No. 219,290 and U.S. Pat. No. 4,638,045, and accordingly, are more suitable for compression molding, injection molding, extruding and other processing methods requiring heat. It is particularly important to note that the amino acid-derived polycarbonates of the present invention are hydrolytically degradable under physiological conditions whereas polycarbonates that are not derived from amino acids are traditionally considered to be hydrolytically stable. Polycarbonates with favorable engineering and mechanical properties that are degradable under physiological conditions are heretofore unknown in the polymer art. The ductile, slowly degrading amino acid-derived polycarbonates of the present invention are capable of being blended with the more brittle and less hydrolytically stable amino acid-derived polyiminocarbonates of the '290 application and U.S. Pat. No. 4,638,048 over all blend ratios (from 0 to 100%) to provide the polymer blends of the present invention, having a broad spectrum of physicomechanical properties.

DETAILED DESCRIPTION OF THE PREFERRED EMBODIMENTS

Figure 1:
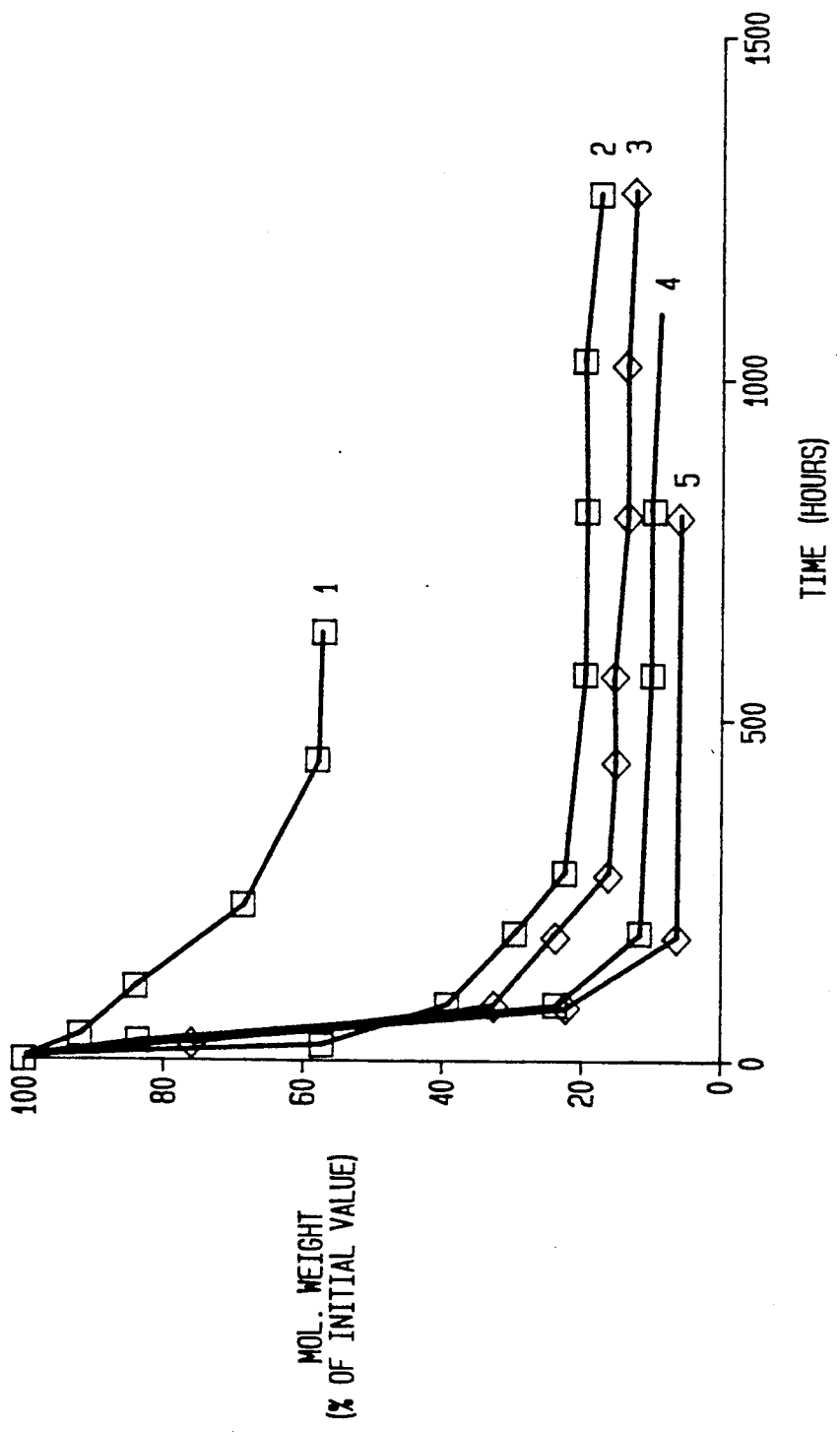
FIG. 1 depicts the degradation profile of several polycarbonate/polyiminocarbonate blends compared to a polyiminocarbonate control.

In the preparation of the polycarbonates of the present invention, amino acid-derived diphenol compounds are employed as the starting materials. Useful amino acid-derived diphenol compounds include those disclosed in U.S. Pat. application Ser. No. 219,290. The disclosure of amino acid-derived diphenol compounds useful to form polycarbonates in said U.S. Pat. application Ser. No. 219,290 is hereby incorporated herein by reference thereto.

The amino acid-derived diphenol compounds can be used in any conventional polymerization process using diphenol monomers, including those processes that synthesize polymers traditionally considered hydrolytically stable and non-biodegradable. Accordingly, the amino acid-derived diphenol compounds of the present invention can not only be used in the preparation of amino acid-derived polycarbonates, they can also be used in the preparation of amino acid-derived polythiocarbonates, polyiminocarbonates and polyethers, as well. As stated above, the amino acid-derived polymers demonstrate hydrolytic instability without sacrificing thermal stability or mechanical properties compared to their counterpart polymers not derived from amino acids.

Preferred amino acid-derived diphenol starting materials for the preparation of the amino acid-derived polycarbonates of the present invention are the amino acid-derived diphenol compounds of Formula II discussed above, with $R_1$ being an alkyl group up to 18 carbon atoms in length.

The particularly preferred amino acid-derived diphenol compound starting materials for the preparation of amino acid-derived polycarbonates according to the present invention are derived from the naturally occurring amino acid L-tyrosine and its analog desaminotyrosine (Dat), which occurs naturally in plants. In this preferred group, the diphenol starting material can be regarded as a pseudodipeptide, properly referred to as a desaminotyrosyl-tyrosine alkyl ester. The most preferred member of the group of desaminotyrosyl-tyrosine alkyl esters is the hexyl ester, referred to as desaminotyrosyl-tyrosine hexyl ester, or DTH.

The amino acid-derived diphenol starting materials are prepared by dicyclohexylcarbodiimide (DCC) mediated coupling reactions in THF following standard procedures of peptide chemistry such as disclosed in Bodanszky, *Practice of Peptide Synthesis* (Springer-Verlag, NY, 1984) at page 145, the disclosure of which is hereby incorporated herein by reference thereto. The diphenols are recrystallized twice, first from 50% acetic acid in water and then from a 20:20:1 ratio of ethyl acetate, hexane and methanol. DTH is prepared by DCC mediated coupling in THF of desaminotyrosine and tyrosine hexyl ester. The crude aklyl ester is obtained as an oil and purified by flash chromatography on silca gel using a 70:30 ratio of chloroform and ethyl acetate as the mobile phase. Crystallization of the pure product is accelerated by crystal seeding. Alkyl esters of tyrosine of up to eight carbon atoms in length are prepared according to the procedure disclosed in J.P. Greenstein and M. Winitz, *Chemistry of the Amino Acids*, (John Wiley & Sons, NY 1961), p. 929, particularly Illustrative Procedure 10–48, the disclosure of all of which is hereby incorporated herein by reference thereto. Alkyl esters of tyrosine greater than eight carbon atoms in length are prepared according to the procedure disclosed in Overell, U.S. Pat. No. 4,428,932, particularly according to the procedure described by the examples, the disclosure of all of which is hereby incorporated herein by reference thereto.

The polycarbonates of the present invention can be prepared by the conventional methods for polymerizing diphenols into same. This involves the reaction of the amino acid-derived diphenol compounds of the present invention with phosgene or phosgene precursors (e.g. diphosgene or triphosgene) in the presence of a catalyst. The amino acid-derived polycarbonates of the present invention may be prepared by any of processes known in the art for polymerization polycarbonates, such as by interfacial polycondensation, polycondensation in a homogeneous phase or by transesterification. The suitable processes, associated catalysts and solvents are known in the art and are taught in Schnell, *Chemistry and Physics of Polycarbonates*, (Interscience, NY, 1964), the teachings of which are incorporated herein by reference thereto.

Preferred amino acid-derived polycarbonates of the present invention, formed by using the amino acid-derived diphenol compound starting materials discussed above, thus include one or more recurring structural units represented by Formula III as described above, with $R_1$ being an alkyl group up to 18 carbon atoms in length and preferably being a hexyl group.

The amino acid-derived polycarbonates of the present invention have weight-average molecular weights above about 50,000 daltons, and preferably above about 100,000 daltons. Molecular weight determinations are calculated from gel permeation chromatography relative to polystyrene standards without further correction. Instrinsic visocosities are above 0.5 dL/g and preferrably in the range of 1.0 to 2.0 dL/g (chloroform, 30° C.).

With the present invention it is now possible to begin with a monomeric starting material such as DTH and synthesize polycarbonates and polyiminocarbonates, two polymers having varying degrees of hydrolytic instability. For example, poly(DTH-carbonate) is strong and tough, slowly degrading and thermally stable. Poly(DTH-iminocarbonate) is very strong and brittle, fast degrading and has limited thermal stability.

The blends of the present invention can be prepared according to conventional techniques for polymer blending. A preferred method for the more temperature-sensitive polyiminocarbonates dissolves preselected ratios of the amino-acid derived polycarbonates and polyiminocarbonates in a solvent such as methylene chloride or chloroform at a concentration of up to about 15% (w/v). The blends are then solvent cast in the desired form and dried to constant weight at high vacuum.

The blends of the present invention of polycarbonates and polyiminocarbonates prepared from the same amino acid-derived monomeric starting material may contain any ratio of polycarbonate and polyiminocarbonate. The preferred levels of each respective polymer in the blends of the present invention will depend upon the requirements of particular end-use applications.

The blend components are completely miscible in all proportions and form macroscopically homogeneous blends from which clear, transparent films are obtained. The tensile strength of the blends does not vary significantly with polyiminocarbonate content, although the ductility and hydrolytic stability of the blends decrease as the polyiminocarbonate content increases.

Accordingly, a family of polymers is provided, suitable for a variety of end-use applications, and derived from the same monomeric starting material. While polymer selection will occur on the basis of properties required by the end-use application, it is also anticipated that the polymers will be combined in specific articles on the basis of their respective properties. In addition to blending, one could coat a rapidly-degrading poly(DTH-iminocarbonate) with a poly (DTH-carbonate) layer to obtain a strong and tough article that slowly degrades at first, but once degradation is initiated, rapidly disintegrates.

The amino acid-derived polycarbonates obtained form resins which can be worked-up by known methods commonly employed in the field of synthetic resins to produce a large variety of different articles with valuable physical and chemical properties, all derived from the same tissue compatible monomer. Preferred amino acid-derived polycarbonates for use in medical applications include poly(DTH carbonate). These polymers are evaluated by well-known tests such as subcutaneous implantations in rats to confirm that they hydrolyze in vivo without significant levels of irritation or inflammation at the subcutaneous implantation sites. Articles made of such polymers are useful, inter alia, as biomedical prosthesis and implants.

The following examples illustrate the present invention and is not intended to limit the same. The example uses the following materials, solvents and measurement procedures.

MATERIALS

Bisphenol A is available from Shell Chemical Company of Houston, TX. Tyramine, L-tyrosine, 3-(4-hydroxyphenyl)-propionic acid (desaminotyrosine), dicyclohexyl carbodiimide (DCC), hexanol, pyridine, methylene chloride, and tetrahydrofuran (THF) and the other solvents are available from Aldrich Chemicals of Milwaukee, WI. Phosgene is available from Fluka of Switzerland. These materials are used without further purification, except THF which is freshly distilled from sodium benzophenone prior to use.

MOLECULAR WEIGHT MEASUREMENTS

GPC data are obtained with a Perkin-Elmer HPLC/GPC system consisting of a Model 410 pump, Perkin-Elmer Model LC-235 diode array UV detector, a Waters Model 410 refractive index detector, and the Perkin-Elmer Model 3600 computerized data station. Two PL-GEL GPC columns (300 mm × 7.7 mm, particle size 5 micron, pore size $10^3$ angstrom and $10^5$ angstrom, respectively) are placed in series and operated at a flow rate of 1.0 ml of THF/min. at room temperature. Data are collected relative to polystyrene standards.

Spectroscopy

FT-IR spectra were recorded on a Matson Cygnus 100 spectrometer. Polymer samples were dissolved in methylene chloride and films were cast directly onto NaCl plates. All spectra were collected after 60 scans at 4 $cm^{-1}$ resolution UV/Vis spectra were recorded on a Perkin-Elmer Lambda 3B spectrophotometer. NMR spectra were recorded on a Varian VXR-200 spectrometer.

Solvent Casting

Polymer films were cast in trimethylsilyl coated glass molds from membrane filtered 15% (w/v) methylene chloride or chloroform solutions. The molds were kept partly covered with aluminum foil and stored for 24 h at room temperature. Transparent films were obtained which were dried to constant weight in high vacuum. Rectangular strips or round disks were cut from the films.

Mechanical Properties

The mechanical properties of thin, solvent cast polymer films were measured on an Instron Tensile Tester according to ASTM standard D882083. In all cases, tensile values were calculated from the average of at least four measurements obtained from four separate specimens per polymer sample. Since unoriented, non-crystalline films were used, the results are representative of the bulk properties of the polymers.

Hydrolytic Degradation Studies

Disks (2.3 cm × 1.1 cm × 0.05 cm, approximately 150 mg) were cut from solvent cast films. The disks were incubated at 37° C. in phosphate buffer (0.1 M, pH 7.4). The degradation process was followed by recording the weight change of individual disks, by measuring the residual polymer molecular weight after various intervals of exposure to the buffer solution and by FT-IR analysis of partly degraded samples.

EXAMPLE 1

Poly(DTH carbonate) is prepared as follows:

14.69 g of DTH (35.5 mmoles) is placed into a 250 ml flask. After addition of 75 ml of dry methylene chloride and 10.8 ml of anhydrous pyridine, a pale yellow solution is obtained. At room temperature, 22.5 ml of a 1.94 M solution of phosgene in toluene (43.6 mmoles) is added slowly to the vigorously stirred solution over a period of about 90 minutes. Stirring is continued for an additional 120 minutes. Thereafter, the reaction mixture is diluted with 500 ml of methylene chloride, transferred into a separatory funnel and extensively extracted with 0.2 N aqueous HCl. The organic phase (containing the polymer) is then dried over magnesium sulfate and concentrated to 150 ml. The polymer is precipitated by slowly adding the concentrated solution into 750 ml of hexane.

The resulting poly(DTH carbonate) is a white slightly tinged material that is readily soluble in most strong organic solvents such as chlorinated hydrocarbons, THF and dimethylformamide (DMF). It is insoluble in water, alcohols, and swells in acetone. The solution has a slight yellow tinge. Strong, transparent films are readily obtained from 10–15% solutions in chlorinated hydrocarbons by solvent casting. Before high temperature processing, however, the polymer should be carefully dried in order to avoid the hydrolytic cleavage of the ester side claim linkages.

The polymer has a weight-average molecular weight of 658,000 daltons and a number average molecular weight of 269,000 daltons as calculated from gel permeation chromatography in DMF relative to polystyrene standards without further corrections. The intrinsic viscosity measured in chloroform at 30° C. is 1.098 dL/g. The structure of the polymer is confirmed by IR and NMR spectroscopy.

EXAMPLES 2-8

Poly(DTH carbonate) is prepared as described in Example 1 and blended with poly(DTH iminocarbonate), prepared by solution polymerization according to the disclosure of the '290 application. Blends of various ratios are prepared, as shown in Table I, with Examples 2 and 8 serving as controls. The polyiminocarbonate has a weight-average molecular weight of 103,000 daltons as calculated from gel permeation chromatography in DMF relative to polystyrene standards without further corrections.

Films of the polymers and polymer blends were solvent cast and the mechanical properties and degradation profiles of the films were measured. The mechanical properties are recorded in Table I and the degradation profiles are depicted in FIG. 1.

TABLE I

| Example | % Polycarbonate | Tensile Strength (kg/cm$^2$) | Elongation (% at break) |
|---|---|---|---|
| 2 | 0 | 400 | 7 |
| 3 | 10 | 369 | 5 |
| 4 | 50 | 355 | 9 |
| 5 | 90 | 361 | 12 |
| 6 | 95 | 394 | 25 |
| 7 | 98 | 401 | 46 |
| 8 | 100 | 335 | 120 |

The tensile strength of the polymer blends shows no systematic variation. Ductility, however, is strongly dependent upon polyiminocarbonate content, with only 2% polyiminocarbonate content reducing the ductility of the blends significantly. Fifty percent blends are about as brittle as pure polyiminocarbonate.

With reference to the degradation profiles of FIG. 1, blends containing 95% 1, 90% 2, 50% 3 and 10% 4 polycarbonate are compared to a polyiminocarbonate control 5. The presence of polyiminocarbonate has a strong effect on the degradation profile of the blends. A steady decrease in the molecular weight of the blend as a whole is observed, indicating that both the polyiminocarbonate and polycarbonate fractions are degrading simultaneously. In all blends, the initial phase of rapid degradation (typical of polyiminocarbonates) is followed by a prolonged phase of slow degradation (typical of polycarbonates). The extent of the initial rapid phase of blend degradation is related to the proportion of iminocarbonate present, with even small proportions of polyiminocarbonate present having a significant effect. Blending with polyiminocarbonate therefore appears to be an efficient way to increase the rate of polycarbonate degradation.

The foregoing description and examples should be understood by one of illustration rather than by one of limitation of the present invention as defined in the claims. As will be appreciated, numerous variations and combinations of the features set forth within the foregoing description and examples can be utilized without departing from the present invention.

We claim:

1. A diphenol compound comprising an amino acid derivative of the formula:

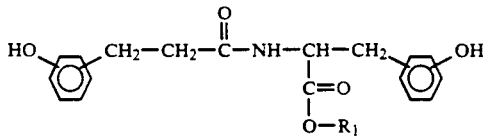

wherein $R_1$ is an alkyl group up to 18 carbon atoms in length.

2. The diphenol compound of claim 1, wherein $R_1$ is —(CH$_2$)$_5$—CH$_3$.

* * * * *

UNITED STATES PATENT AND TRADEMARK OFFICE
CERTIFICATE OF CORRECTION

PATENT NO. : 5,099,060
DATED : March 24, 1992
INVENTOR(S) : Kohn et al.

It is certified that error appears in the above-identified patent and that said Letters Patent is hereby corrected as shown below:

Column 2, line 61, "unacceptable" should read --unacceptably.--.

Column 5, line 59, "silca" should read --silica--.

Column 6, line 13, "any of processes" should read --any of the processes--.

Column 7, line 54, "pore size 103" should read --pore size $10^3$--.

Column 7, line 65, after "resolution" and before "UV/Vis" insert --.--.

Signed and Sealed this

Twenty-sixth Day of October, 1993

Attest:

BRUCE LEHMAN

Attesting Officer         Commissioner of Patents and Trademarks